United States Patent [19]

Murthy et al.

[11] Patent Number: 4,793,998

[45] Date of Patent: Dec. 27, 1988

[54] STABILIZED DRUG COMPOSITIONS

[75] Inventors: Kuchi S. Murthy, Morris Plains; Michael R. Harris, Hackettstown; Gerard C. Hokanson, Long Valley; Robert G. Reisch, Jr., Haledon; Frank Waldman, Wayne; Mahdi B. Fawzi, Flanders, all of N.J.

[73] Assignee: Warner-Lambert Company, Morris Plains, N.J.

[21] Appl. No.: 921,931

[22] Filed: Oct. 20, 1986

[51] Int. Cl.$^4$ .................... A61K 9/68; A61K 31/27; A61K 31/40; A61K 31/195

[52] U.S. Cl. .................... 424/440; 424/457; 424/464; 424/468; 514/307; 514/310; 514/419; 514/423; 514/970

[58] Field of Search .............. 424/440, 464, 465, 476, 424/482, 457, 468; 514/307, 310, 419, 423, 970

[56] References Cited

U.S. PATENT DOCUMENTS

| | | | |
|---|---|---|---|
| 3,697,641 | 10/1972 | Abrams | 424/440 |
| 4,656,188 | 4/1987 | Veber et al. | 514/562 X |
| 4,666,705 | 5/1987 | De Crosta et al. | 424/482 |

*Primary Examiner*—Michael Lusignan
*Attorney, Agent, or Firm*—Howard Olevsky; Ronald A. Daignault

[57] ABSTRACT

The cyclization and hydrolysis of certain ACE inhibitors is minimized when they are formulated with a stabilizer and at least one lubricant and/or excipient.

21 Claims, No Drawings

STABILIZED DRUG COMPOSITIONS

BACKGROUND

Certain Angiotensin Converting Enzyme (ACE) inhibitors are unstable in that, they are highly susceptible to decomposition by cyclization hydrolysis and oxidative attack. It is believed that one or more of these types of decomposition causes the discoloration which results when these compounds are formulated into pharmaceutical dosage forms. Antihypertensive compounds, such as quinapril and enalapril, undergo autocyclization to the undesirable diketopiperazine. In addition, they may form diacids via hydrolysis or may undergo oxidation leading to discoloration. It is their conversion to these sometimes unwanted substances which can result in lessened drug effectiveness in compositions containing this type of drug.

THE INVENTION

It has been discovered that the degradation due to cyclization and hydrolysis which has been commonly associated with dosage forms containing, e.g., quinapril, can be overcome via the use of certain quantities of ascorbic acid alone or ascorbic acid in combination with one or more of fumaric acid, citric acid and maleic acid in the formulations.

In addition, the effect of the ascorbic acid is maximized when certain lubricants, e.g., Sterotex ®, and/or talc, are used in combination therewith.

Furthermore, the overall stability of the final pharmaceutical formulation is enhanced when specific types of excipients, such as mannitol and lactose, are included therein.

ADVANTAGES

The compositions of the invention have several advantages over compositions which do not contain the stabilizing additive(s) discussed herein. Principally, the active ingredients or drugs contained therein are virtually preserved from cyclization and hydrolysis. In addition, the discoloration which sometimes occurs when ACE inhibitors of this class are formulated and allowed to stand for significant periods of time is minimized or eliminated completely. Thus, a stable tabletted quinapril formulation can be produced which will undergo no detectable oxidative discoloration.

In addition to having greater storage stability, the instant formulations are rendered more suitable for use in drug combinations.

These and other advantages of the invention will become apparent from a consideration of the following description of the invention.

DESCRIPTION OF THE INVENTION

The invention deals with:
I. A pharmaceutical composition which contains:

(a) a drug component which comprises an ACE inhibitor which is susceptible to cyclization and hydrolysis.

(b) an amount of a stabilizer component or components suitable to retard cyclization and/or hydrolysis, and II. A process for stabilizing an ACE inhibitor drug which comprises the step of contacting the drug with:

(a) an amount of stabilizer(s) suitable to retard cyclization and/or hydrolysis.

III. A method of making a pharmaceutical dosage form which comprises the step of including in the formulation suitable amounts of:

(aa) an ACE inhibitor, and (b) stabilizers which contains ascorbic acid alone or ascorbic acid in combination with organic acids such as fumaric, maleic and/or citric acid as a cyclization and hydrolysis inhibitors.

Preferably, the compositions and processes made and used in accordance with the invention will also contain one or more substances which do not interfere with the function of the ascorbic acid component. Generally, lubricants, such as hydrogenated vegetable oils and talc, and/or excipients, such as mannitol and lactose, are suitable.

Drug Component(s)

The compositions of the invention contain at least one ACE inhibitor and, optionally, one or more other medicament drugs or beneficial substances.

The ACE inhibitors which can be used in the invention are any of a group of well-known compounds which have antihypertensive properties.

One preferred group of compounds includes compounds conforming to the general formula

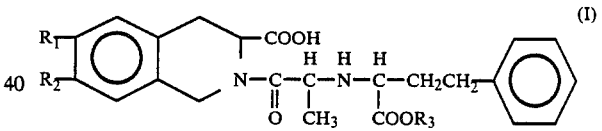

wherein $R_1$ and $R_2$ are —H or —$OC_nH_{2n+1}$, $R_3$ is —H or —$C_nH_{2n+1}$, and $n=1$ to 5. Preferably $R_1$ and $R_2$ are the same. Most preferably, $R_1$ and $R_2$ are both —H or —$OCH_3$ same. Most preferably, $R_1$ and $R_2$ are both —H or —$OCH_3$ and $R_3$ is —H or —$C_2H_5$.

Compounds of this type are disclosed in U.S. Pat. No. 4,344,949, the disclosure of which is hereby incorporated by reference.

Thus, one preferred group of compounds include quinapril and components of formulas II through IV.

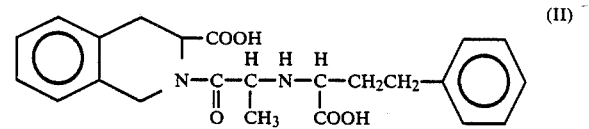

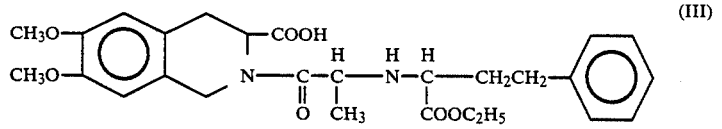

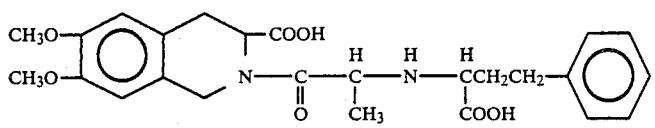

(IV)

Mixtures are operable.

Quinapril, is highly preferred. Its structure is:

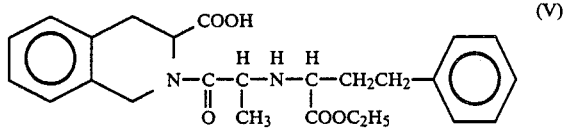

(V)

The dotted line shown represents the bond which forms when the compound cyclizes to a diketopiperazine.

It is believed that this unwanted piperazine occurs when quinapril and similar compounds are stored without one or more stabilizers.

Another preferred group of compounds include those of formula VI:

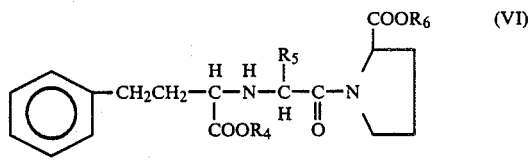

(VI)

wherein $R_4$ and $R_5$ are $C_{1-4}$ alkyl, and $R_6$ is —H or $C_{1-4}$ alkyl. Enalapril is preferred.

The total drug content of the final composition will be about 1 to about 70%, preferably from about 3% to about 20%. Generally, one or more ace inhibitor(s) will be the only drug present.

All percentages stated herein are weight percentages based on total composition weight, unless otherwise stated.

The daily dosages of the pharmaceutical preparations of the invention depend upon the nature of the dosage form, the nature of the drug(s) and the type and extent of any interactive(s), in drug combinations. Thus, the therapeutic needs of the individual patient and the desires of the prescribing physician dictate the dosage levels to be employed.

In general, however, the manufacturer's specifications for any drug or drug combination are useful guides to administration. *The Physician's Desk-Reference* or other suitbble publication can be consulted to ascertain appropriate dosage levels.

Nonetheless, typical dosage levels for quinapril and enalapril are from about 1 mg to about 80 mg per dosage.

Suitable categories of drugs that may be employed in addition to ACE inhibitors in the instant compositions may vary widely and generally represent any stable drug combination.

Illustrative categories and specific examples include:

(a) Diuretics, such as hydrochlorothiazide.

(b) Antitussives, such as dextromethorphan, dextromethorphan hydrobromide, noscapine, carbetapentane citrate, and chlophedianol hydrochloride;

(c) Antihistamines, such as chlorpheniramine maleate, phenindamine tartrate, pyrilamine maleate, doxylamine succinate, and phenyltoloxamine citrate, (d) Decongestants, such as phenylephrine hydrochloride, phenylpropanolamine hydrochloride, pseudoephedrine, hydrochloride ephedrine; and (e) Various alkaloids, such as codeine phosphate, codeine sulfate and morphine.

(f) Mineral supplements such as potassium chloride and calcium carbonates.

The medicaments and/or other beneficial substances to be used herein may be selected from a wide variety of substances and pharmaceutically acceptable forms thereof, e.g., their acid addition salts. Both organic and inorganic salts may be used provided the drug maintains its medicament value. Exemplary acid salts include hydrochloride, hydrobromide, orthophosphate, benzoate, maleate, tartrate, succinate, citrate, salicylate, sulfate, acetate, and the like. Mixtures are operable.

One preferred group of drugs to be used in combination with ACE inhibitors includes: beta-blockers, diuretics, calcium blockers, and the like.

Stabilizer(s)

The cyclization and hydrolytic instability which are exhibited by certain of the drugs discussed above can be overcome via the use of an appropriate quantity of an ascorbic acid-containing stabilizer.

While the use of ascorbic acid as an antioxidant for pharmaceuticals is known, its function is an inhibitor of cyclization reactions and hydrolysis is not yet known. While applicants do not intend to be bound by any particular theory, it is believed that the ascorbic acid prevents the cyclization process and, thus inhibits the production of diketopiperazines and other unwanted substances.

The quantity of the stabilizer component to be used will lie between about 1% and 90%, preferably about 10% to about 80%, most preferably about 20% to about 50%. In general, any amount which will effectively retard or prevent degradation of the ace inhibitor component(s) can be used.

It is important to note that the use of ascorbic acid itself in the stabilizer component is critical to the practice of the invention. While it is generally required that the ascorbic acid content of the composition be from about 10% to about 20% for the attainment of hydrolytic and anti-autocyclization stability, the remainder of the stabilizer component may be one or more acids selected from citric, fumaric and maleic acids.

Other stabilizers which contain ascorbic moieties should not be used. Salts and esters of ascorbic acid are not operable.

The exact mechanism for the stabilizing activity of the ascorbic acid-containing stabilizing systems of the invention is not clearly known. However, applicants believe that the ascorbic acid-containing stabilizer functions in at least two ways:

1. The acid(s) inhibits the auto cyclization of compounds such as quinapril by interfering with the formation of the bond which is represented by a dotted line in formula V, above.

2. The acid(s) serves to lower the pH of the composition so that conditions are unfavorable for hydrolysis.

Lubricant(s)

The optional lubricant components to be used in the pharmaceutical products and methods of the invention are substances which are compatible with the ascorbic acid-containing stabilizers. Generally, they are substances which do not contain groups which could significantly interfere with the function of either the ascorbic acid-containing component or the drug component.

It is thought that the presence of readily ionizable moieties in the lubricant component adversely affects the action of the ascorbic acid. Thus, stearic acid and conventional metal salts thereof are not operable lubricants in the instant formulations because they interfere with the ability of the ascorbic acid-containing component to prevent cyclization. One preferred group of lubricants include hydrogenated vegetable oils, e.g., hydrogenated cottonseed oil, and talc. Sterotex ® is a preferred hydrogenated cottonseed oil. Mixtures are operable.

Generally, the quantity of lubricant present will be from about 0.5% to about 10%, preferably about 1% to about 5%.

Excipient(s)

The optional excipients which can be used in the instant compositions are also substances which must be compatible with the ascorbic acid component so that it does not interfere with its function in the composition. Generally, the excipients to be used herein include sugars such as mannitol, lactose, and other sweeteners and carriers which do not adversely affect the function of the other ingredients in the composition. Mannitol, lactose, and other sugars are preferred. Mixtures are operable.

The compositions of the invention may contain carriers, diluents, pigments, binders, colorants, and other additives conventionally used in the production of pharmaceutical products.

The method by which the ingredients are combined —i.e., the technique for processing the products of the invention—is not critical. Any techniques which are appropriate according to the physical and chemical nature of the materials to be treated can be employed.

The percentages in which excipients are used are not critical. In general, their quantities will be consistent with the amount given above for the drug, stabilizer, and lubricant components, i.e., they make up the remainder of the composition.

Dosage Forms

The final form of the pharmaceutical preparations made in accordance with the invention can vary greatly. Thus, tablets, capsules, sachets, sprinklers, pomades, transdermal compositions, buccal preparations, candy compositions, nasal formulations, ocular compositions and the like are contemplated. Orally administrable forms, i.e., tablets, caplets, and capsules, are preferred.

Solid, semi-solid, and liquid formulations can be made. However, solids are highly preferred.

The drug preparations can be adapted for immediate, slow, or sustained release profiles, or any combination of these. Thus a formulation adapted to give an initial loading dosage within 30 minutes followed by sustained release of the remaining drug over 4 to 12 hours is contemplated. Sustained and immediate release formulations are preferred.

EXAMPLES

The following examples illustrate the invention.

EXAMPLE 1

Stable quinapril formulations for use in the production of tablets or capsules will typically contain the following ingredients:

|  | wt. % |
| --- | --- |
| Quinapril HCl | 3–30 |
| Ascorbic Acid | 40–50 |
| Hydrogenated Vegetable Oil or Talc | 2–10 |
| Lactose | Remainder |

Such compositions have been shown to be stable at 45° C. for 1 month.

EXAMPLE 2

Stable quinapril formulations can be made containing the following ranges of ingredients.

| Ingredient | Wt %. |
| --- | --- |
| Quinapril HCl | 3–30 |
| Ascorbic Acid | 10 |
| One or more of Citric, Fumaric, and Maleic Acid | 30–40 |
| Hydrogenated Vegetable Oil or Talc | 2–10 |
| Lactose | Remainder |

These compositions are stable at 45° C. for 1 month.

EXAMPLE 3

One highly preferred composition to be used in accordance with the invention contains:

| Ingredient | Wt % |
| --- | --- |
| Quinapril HCl | 3.6 |
| Ascorbic Acid | 0.0 |
| Lactose | 72.4 |
| Sterotex | 4.0 |

This composition is stable at 60° C. for 10 days; 45° C. for 1 month; and at 80% relative humidity for 1 day. It is administrable at dosage levels of 5 mg to 40 mg 2 times a day.

Reasonable variations, such as those which would occur to a skileed artisan, can be made herein without departing from the scope of the invention.

We claim:

1. A pharmaceutical composition which contains:
   (a) a drug component which comprises from about 1 to about 70% by weight of an ACE inhibitor which is susceptible to cyclization and/or hydrolysis,
   (b) about 1 to about 90% by weight of an ascorbic acid-containing stabilizer to inhibit cyclization and/or hydrolysis with ascorbic acid being at least 10% by weight of the pharmaceutical composition; and optionally,
   (c) one or more components which do not significantly interfere in the function of component (b).

2. The composition of claim 1 wherein (c) is at least one material selected from the group consisting of: excipients and lubricants.

3. The composition of claim 1 wherein (b) contains ascorbic acid and citric acid.

4. The composition of claim 1 wherein (b) contains ascorbic acid and fumaric acid.

5. The composition of claim 1 wherein (b) contains ascorbic acid and maleic acid.

6. The composition of claim 2 wherein (a) is quinapril and, (c) contains a lubricant and an excipient.

7. The composition of claim 6 wherein the lubricant is selected from the group consisting of hydrogenated vegetable oil, talc, and mixtures thereof.

8. The composition of claim 7 wherein the excipient is selected from the group consisting of mannitol and lactose.

9. The composition of claim 8 wherein the lubricant is hydrogenated cottonseed oil.

10. The composition of claim 9 wherein (a) contains at least one additional drug.

11. A tablet containing the composition of claim 10.

12. A tablet containing the composition of claim 10.

13. A candy formulation containing the composition of claim 9.

14. A candy formulation containing the composition of claim 10.

15. A process for stabilizing an ACE inhibitor drug against cyclization and/or hydrolysis which comprises the step of contacting the drug with:
   (a) from about 1 to about 90% of a stabilizer which contains at least 10% by weight of the combination of the stabilizer and drug of ascorbic acid, and, optionally,
   (b) one or more compounds which do not significantly interfere with the function of (a).

16. The process of claim 15 wherein the drug is selected from the group consisting of quinapril, enalapril, and mixtures thereof.

17. The process of claim 16 wherein (b) is selected from the group consisting of lubricants, excipients, and mixtures thereof.

18. The process of claim 17 wherein (b) contains a lubricant and an excipient.

19. The method of claim 18 wherein the lubricant is selected from the group consisting of: hydrogenated vegetable oil, talc, and mixtures thereof.

20. The method of claim 19 wherein the excipient is selected from the group consisting of mannitol and lactose.

21. The method of claim 20 wherein the lubricant is hydrogenated cottonseed oil.

* * * * *